(12) United States Patent
Rechner (10) Patent No.: US 8,617,834 B2
(45) Date of Patent: Dec. 31, 2013

(54) THROMBOPLASTIN REAGENT WITH LONG-TERM STABILITY

(75) Inventor: Andreas Rechner, Marburg (DE)

(73) Assignee: Siemens Healthcare Diagnostics Products GmbH, Munich (DE)

(*) Notice: Subject to any disclaimer, the term of this patent is extended or adjusted under 35 U.S.C. 154(b) by 643 days.

(21) Appl. No.: 12/335,391

(22) Filed: Dec. 15, 2008

(65) Prior Publication Data

US 2009/0162880 A1    Jun. 25, 2009

(30) Foreign Application Priority Data

Dec. 21, 2007   (DE) .................. 10 2007 062 323

(51) Int. Cl.
*C12Q 1/56* (2006.01)
*C12Q 1/00* (2006.01)

(52) U.S. Cl.
USPC ................................. 435/13; 435/4

(58) Field of Classification Search
USPC ....................................... 435/13, 4
See application file for complete search history.

(56) References Cited

U.S. PATENT DOCUMENTS

| | | | |
|---|---|---|---|
| 3,183,159 A | 5/1965 | Singher et al. | |
| 3,486,981 A | 12/1969 | Speck | |
| 3,522,148 A | 7/1970 | Adam, Jr. | |
| 3,980,432 A | 9/1976 | Trobisch et al. | |
| 4,416,812 A | 11/1983 | Becker et al. | |
| 6,100,072 A * | 8/2000 | Brucato et al. | 435/69.7 |
| 7,622,437 B2 * | 11/2009 | Morrissey et al. | 514/1.1 |
| 7,682,808 B2 * | 3/2010 | Morrissey et al. | 435/13 |
| 2003/0157582 A1 | 8/2003 | Roisin et al. | |
| 2004/0086420 A1 * | 5/2004 | MacPhee et al. | 422/22 |
| 2010/0297117 A1 * | 11/2010 | Sloey et al. | 424/133.1 |

FOREIGN PATENT DOCUMENTS

| | | |
|---|---|---|
| EP | 0 020 895 | 1/1981 |
| EP | 420 332 A2 | 4/1991 |
| EP | 585 987 A1 | 3/1994 |
| EP | 942 284 A2 | 9/1999 |
| JP | JA2006-296379 | 11/2006 |
| WO | WO 2006/009373 A1 | 1/2006 |

OTHER PUBLICATIONS

Lee et al., "Tissue Factor Inhibitory Flavonoids from the Fruits of *Chaenomeles sinensis*" *Arch. Pharm. Res.* 25: 842-50 (2002).
Macheix et al., "The Main Phenolics of Fruits" in Fruit Phenolics, CRC Press, Boca Raton, USA, chapter 1 (1990).
Stampfuss et al., "Green Tea Catechins Containing a Galloyl Group in the 3' Position Inhibit Tissue Factor-Induced Thrombin Generation" *Thromb. Haemost.* 93:1200-01 (2005).
Volpi, I., "L'effetto Emostatico e Vasoprotettivo Dell'associazione Tromboplastina-quercetina in Campo Ostetrico e Ginecologico" *Minerva Ginecologica* 11:210-12 (1959).
English translation of abstract for JA2006-296379.

* cited by examiner

*Primary Examiner* — Karen Cochrane Carlson
*Assistant Examiner* — Natalie Moss
(74) *Attorney, Agent, or Firm* — Finnegan, Henderson, Farabow, Garrett & Dunner, LLP (57) ABSTRACT

The present invention is in the area of coagulation analysis and relates to a reagent which is based on recombinant or native tissue factor and phospholipids and which can be stabilized by adding a polyphenol.

22 Claims, 5 Drawing Sheets

THROMBOPLASTIN REAGENT WITH LONG-TERM STABILITY

This application claims the benefit of German Application No. 10 2007 062 323.4, filed Dec. 21, 2007, which is incorporated herein by reference.

The present invention is in the area of coagulation analysis and relates to a re-agent which is based on recombinant or native tissue factor and phospholipids and which can be stabilized by adding a polyphenol.

Tissue factor (thromboplastin) is a transmembrane protein with essential importance for blood coagulation. It is expressed by cells which are not normally in contact with flowing blood, such as, for example, by cells in the subendothelium (smooth muscles) and by cells which surround blood vessels (e.g. fibroblasts). In the event of damage to blood vessels, however, the tissue factor-expressing cells come into contact with factor VII, a procoagulant blood coagulation factor which circulates in the blood. Tissue factor and factor VII form a complex in the presence of calcium, and there is a thousand-fold increase in the activity of factor VII (F VII>F VIIa). The complex of tissue factor and factor VIIa catalyzes, in the presence of phospholipids and calcium, the conversion of the inactive blood coagulation factor X into activated factor Xa and thus expedites the coagulation process. Tissue factor, together with factor VII, forms the so-called extrinsic pathway of blood coagulation, by which an injury to blood vessels is to be neutralized by the fastest possible blood coagulation.

Various in vitro test methods have been developed in coagulation analysis, allowing determination of whether the blood or plasma of a patient is able to coagulate satisfactorily or whether a coagulation disorder is present. In the event of a coagulation disorder, it is frequently necessary to obtain more precise information about the cause of the disorder present, in order to be able to select optimal therapeutic measures. Tissue factor is used as activator for investigating various subfunctions of blood coagulation, especially for investigating the extrinsic system of blood coagulation. The best known use of tissue factor as coagulation activator is the so-called Quick's test for determining the prothrombin time (PT). In Quick's test and its variants, normally a plasma sample is mixed with a mixture of tissue factor, phospholipids and calcium ions, and the time from the instant of mixing until fibrin formation is perceptible is measured in seconds. In coagulation tests in which chromogenic substrates are used, alternatively the time from the instant of mixing until a particular change in absorption is reached is measured. Tissue factor is also employed in other test methods which serve not to determine a coagulation time but to determine individual components of the coagulation system such as, for example, the endogenous thrombin potential (ETP) (EP 420 332 A2). Tissue factor can in principle be used in all tests concerned with components of extrinsic coagulation.

The thromboplastin reagent (tissue factor reagent) has a central importance for the particular test. Normally, a thromboplastin reagent contains tissue factor together with procoagulant phospholipids. The tissue factor is either obtained as tissue extract from various organs (e.g. brain, placenta, lung) of various species (e.g. rabbit, human, cattle) or is produced recombinantly. Numerous methods for obtaining tissue factor and for producing thromboplastin reagents are known in the prior art, and a large number of thromboplastin reagents is commercially available.

At present, most purchasable thromboplastin reagents are marketed in freeze-dried form and must therefore be dissolved before use in a reconstitution medium, e.g. in distilled water or a buffer solution. The reason for this is the lack of stability of the reagents in the liquid state. The disadvantage of reagents which are provided in freeze-dried form is not only that manufacturers and users must carry out additional time-consuming and costly steps in the methods (lyophilization and reconstitution), but also that these additional measures entail the risk of errors occurring and possibly impairing the quality of the reagent. Liquid reagent formulations ready for use are therefore desirable. One problem in providing liquid thromboplastin reagents is, however, their lack of stability. The stability of a thromboplastin reagent may be understood to be for example the constancy of the prothrombin time for a defined plasma, e.g. a normal plasma over time. Ideally, a thromboplastin reagent should maintain its specifications, or in the most favorable case the properties and characteristics as at the instant of its manufacture, over the duration of its storage or use.

Various strategies for stabilizing liquid thromboplastin reagents are described in the prior art. EP 942 284 A2 describes a liquid thromboplastin reagent which is based on recombinant tissue factor and which is stabilized by combined addition of ascorbic acid and a serum albumin. U.S. Pat. No. 3,522,148 describes a liquid thromboplastin reagent which is based on (natural) tissue factor extracted from tissue and which is stabilized by addition of certain sodium or calcium salts. EP 585 987 A1 describes another liquid thrombo-plastin reagent which is based on natural tissue factor and which is stabilized by addition of various stabilizers such as albumin or polyethylene glycol, and various substances having antimicrobial activity, such as sodium azide or antibiotics.

The present invention was based on the object of providing an alternative method for stabilizing a liquid thromboplastin reagent. This object is achieved by providing the methods and items according to the invention which are described in the claims. The object is achieved in particular by adding at least one water-soluble polyphenol which has at least one catechol function to a thromboplastin reagent which comprises tissue factor and phospholipids.

Polyphenols are aromatic compounds comprising two or more phenolic hydroxyl groups in the molecule (see also Macheix, Jean-Jaques et al.: Fruit Phenolics. CRC Press, Inc., Boca Raton, USA, 1990, chapter 1). Natural polyphenols occur in plants as coloring matter (anthocyanins), flavor substances and tannic acids (tannins). Of these mostly bioactive, so-called secondary plant products, far more than 8000 different ones are currently known. Their functions in the plant extend from protection from herbivorous pests and infestation by bacteria or fungi through attraction of insects for pollination by their color (e.g. in the flowers).

The term "catechol function" means the presence of two hydroxyl groups in ortho positions on an aromatic ring of the polyphenol, i.e. the presence of in each case one hydroxyl group at two directly adjacent C atoms of an aromatic ring (e.g. in the 1,2 position, 2,3 position, 3,4 position, etc., such as, for example, in 3,4-dihydroxybenzoic acid).

Suitable polyphenols in the context of the present invention must have at least one catechol function. They may have more than one catechol function, in which case the catechol functions may be present either on the same aromatic ring or on different aromatic rings of the polyphenol. For example, two catechol functions may be present in such a way that one aromatic ring has three hydroxyl groups in ortho positions (e.g. in the 3,4,5 position such as, for example, gallocatechin) or that two aromatic rings of the compound each have one catechol function (such as, for example, rosmarinic acid). Three catechol functions may for example be present by a first aromatic ring having three hydroxyl groups in ortho positions, and a second aromatic ring having two hydroxyl groups in ortho positions (such as, for example, catechin gallate) or through three aromatic rings of the compound each having one catechol function (such as, for example, procyanidin trimer composed of three catechin molecules). Corresponding statements apply to polyphenols having more than three catechol functions. Epigallocatechin gallate for example has four catechol functions, specifically through two aromatic rings each having three hydroxyl groups in ortho positions.

The flavonoids and the phenolic acids form the two most important subgroups of polyphenols. In addition, the substance groups of stilbenes, coumarins, xanthones, lignins and tannins are also included in the polyphenols. The flavonoids are a group of water-soluble plant coloring matters all of which are derived from the basic chemical structure of flavane (see also Macheix, Jean-Jaques et al.: Fruit Phenolics. CRC Press, Inc., Boca Raton, USA, 1990, chapter 1). Most flavonoids are bound to glucose or rhamnose, which is why they are also called glycosides. Only the flavan-3-ols and the proanthocyanidins are not bound to sugar molecules (=aglycones).

The flavonoids are further divided according to structural properties into:
- flavonols (e.g. quercetin, rutin, kaempferol, myricetin and derivatives thereof),
- flavan-3-ols (e.g. catechin, gallocatechin, epicatechin, epigallo-catechin gallate),
- procyanidin (polymeric flavan-3-ols),
- flavones (e.g. luteolin, apigenin, morin and derivatives thereof),
- flavanones (e.g. hesperetin, naringenin, eriodictyol and derivatives thereof, such as, for example, hesperidin or naringin),
- isoflavones (e.g. genistein, daidzein and derivatives thereof),
- anthrocyanins (e.g. cyanidin, delphinidin, malvidin, pelargonidin, peonidin, petunidin and derivatives thereof).

It has been reported that galloylated flavan-3-ols such as epigallocatechin gallate have inhibitory effects in vitro on thrombin generation [Stampfuss et al. (2005) Green tea catechins containing a galloyl group in the 3' position inhibit tissue factor induced thrombin generation. Thromb Haemost 93: 1200-1201].

The phenolic acids are chemical compounds which can be divided into the groups of hydroxybenzoic acids and of hydroxycinnamic acids (see also Macheix, Jean-Jaques et al.: Fruit Phenolics. CRC Press, Inc., Boca Raton, USA, 1990, chapter 1). The hydroxybenzoic acids include inter alia salicylic acid, gallic acid, protocatechuic acid and vanillic acid, and derivatives thereof such as, for example, 3,4-dihydroxybenzoic acid. The best-known hydroxycinammic acids include for example caffeic acid, ferulic acid, synapic acid and coumaric acid, and derivatives thereof such as, for example, caffeoyl glucose, rosmarinic acid, ferulylquinic acid. In nature, phenolic acids occur in a similar manner to the flavonoids almost exclusively in bound form. Esters with organic acids or glycosides such as, for example, chlorogenic acid or caftaric acid are most common.

The present invention relates to a method for stabilizing thromboplastin reagents, i.e. aqueous solutions which comprise tissue factor and phospholipids. It has been found that addition of one or more polyphenols, with at least one polyphenol being water-soluble and having at least one catechol function, increases the stability of an aqueous solution comprising tissue factor and phospholipids. Thromboplastin reagents stabilized according to the invention provide even after storage at +2° C. to +8° C. for 12 months prothrombin time (PT) measurements which are less than 25% different from the PT measurement at the start of the period. Accelerated storage at +37° C. for 8 weeks provides a quicker estimate of whether a storage stability at +2° C. to +8° C. over a period of 12 or more months can be expected. If a stabilized thromboplastin reagent on storage at +37° C. over a period of 4 weeks provides prothrombin time (PT) measurements which differ by less than 25% from the PT measurement at the start of the period, it can be expected that the reagent is stable on storage at the temperature of +2° C. to +8° C. over a period of 12 or more months.

In a preferred embodiment of the method of the invention, at least one water-soluble polyphenol which has at least one catechol function is added to the thromboplastin reagent in such a way that the polyphenol is present in the reagent in a final concentration of from 0.15 to 10 mM, particularly preferably from 0.5 to 2 mM.

In a specific embodiment of the method of the invention, two or more water-soluble polyphenols, of which at least one has at least one catechol function, are added to the thromboplastin reagent. Preferably two water-soluble polyphenols are added to the thromboplastin reagent, with both polyphenols having at least one catechol function. More preferably, the two or more polyphenols are added to the thromboplastin reagent in such a way that each of the polyphenols is present in the reagent in a final concentration of from 0.15 to 10 mM, particularly preferably from 0.5 to 2 mM. Preferred combinations of a plurality of polyphenols include the combination of chlorogenic acid and catechin or the combination of chlorogenic acid and rutin.

In a specific embodiment of the method of the invention, at least one water-soluble polyphenol which has at least one catechol function and is derived from the group of flavonoids is used for the stabilization. Suitable flavonoids which are water-soluble and have at least one catechol function are for example:
- quercetin, rutin, myricetin and glycosides thereof, which belong to the subgroup of flavonols;
- catechin, gallocatechin, epicatechin, epigallocatechin gallate, which belong to the subgroup of flavan-3-ols;
- procyanidins which belong to the subgroup of polymeric flavan-3-ols;
- luteolin and glycosides thereof, which belong to the subgroup of flavones; and
- cyanidin, delphinidin, petunidin and glycosides thereof, which belong to the subgroup of anthocyanins.

In a particularly preferred embodiment of the method of the invention, at least catechin or epicatechin is used for the stabilization.

In a further specific embodiment of the method of the invention, at least one water-soluble polyphenol which has at least one catechol function and is derived from the group of phenolic acids is used for the stabilization. Suitable phenolic acids which are water-soluble and have at least one catechol function are for example:
- gallic acid, protocatechuic acid (3,4-dihydroxybenzoic acid) and the esters or glycosides thereof, which belong to the subgroup of hydroxybenzoic acids; and
- caffeic acid, chlorogenic acid, caftaric acid, caffeoylglucose, rosmarinic acid and the esters or glycosides thereof, which belong to the subgroup of hydroxycinnamic acids.

In a particularly preferred embodiment of the method of the invention, at least chlorogenic acid is used for the stabilization.

In a further embodiment of the method of the invention, in addition L-ascorbic acid and/or polyethylene glycol- and/or a substance having antimicrobial activity is added to the thromboplastin reagent for further stabilization. The amount of L-ascorbic acid preferably added is such that it is present in a final concentration of from 0.1 to 10 mM, particularly preferably from 0.5 to 1 mM, in the reagent. The amount of polyethylene glycol preferably added is such that it is present in a final concentration of from 0.1 to 5% (w/v), particularly preferably from 0.25 to 1% (w/v), in the reagent. Particularly preferred substances having antimicrobial activity are sodium azide and thymol. The amount of sodium azide preferably added is such that it is present in a final concentration of from 0.01 to 1% (w/v), particularly preferably of 0.1% (w/v) in the reagent.

The method of the invention is suitable both for stabilizing thromboplastin reagents which comprise recombinant tissue factor (human or animal, especially rabbit) together with natural and/or synthetic phospholipids, and for stabilizing thromboplastin reagents which comprise natural human or animal (e.g. rabbit, bovine) tissue factor from tissue extracts (e.g. from brain, placenta, lung) together with natural and/or synthetic phospholipids.

The present invention further relates to a reagent or an aqueous solution for use as thromboplastin reagent, which comprises tissue factor and phospholipids, and at least one water-soluble polyphenol which has at least one catechol function. The at least one polyphenol is preferably present in the reagent in a final concentration of from 0.15 to 10 mM, particularly preferably 0.5 to 2 mM. A preferred embodiment of a reagent of the invention additionally comprises calcium ions. Further reagent embodiments of the invention can be obtained by the various embodiments of the method of the invention described above. The reagent may be provided as liquid reagent or else as lyophilizate which can be reconstituted in water or buffer.

The present invention further relates to the use of a thromboplastin reagent of the invention in an in vitro method for determining a coagulation parameter in a patients sample, especially for determining a coagulation parameter from the group of prothrombin time (PT, also Quick's test) and variants thereof and endogenous thrombin potential (ETP). The reagent of the invention is suitable for use as activator of the coagulation cascade, for example in test methods based on detection of a fibrin clot, as well as in chromogenic or fluorogenic test methods.

The present invention further relates to a test kit, in particular for carrying out an in vitro method for determining a coagulation parameter, where the test kit comprises at least one thromboplastin reagent stabilized according to the invention. In the case where the thromboplastin reagent of the invention is present as lyophilizate in the kit, the kit preferably comprises a suitable reconstitution medium (e.g. distilled water or a buffer solution). A test kit which comprises a container with a liquid thromboplastin reagent is preferred.

The following examples serve to illustrate the present invention and are not to be understood as restriction.

EXAMPLE 1

Determination of the Stability of a Thromboplastin Reagent Stabilized with Catechin During Storage at +2-+8° C. for 12 Months A lyophilized thromboplastin reagent which comprised recombinant human tissue factor, synthetic phospholipids and calcium ions was reconstituted with distilled water at time to, and the following substances were added in the stated final concentration to the dissolved reagent:

1. no further addition
2. 0.1% (w/v) sodium azide
3. 0.1% (w/v) sodium azide + 1% (w/v) PEG
4. 0.1% (w/v) sodium azide + 1% (w/v) PEG + 2 mM ascorbic acid
5. 0.1% (w/v) sodium azide + 1% (w/v) PEG + 1 mM catechin
6. 0.1% (w/v) sodium azide + 1 mM catechin The various reagents were employed in an automatic prothrombin time test (PT test) in a BCT® coagulometer (Behring Coagulation Timer, Dade Behring Marburg GmbH, Marburg, Germany). The sample used was a defined reference plasma (calibrator 4 of the PT-Multi Calibrator kit, Dade Behring Marburg GmbH, Marburg, Germany). Sample and reagent were in each case preheated to 37° C. and finally mixed. The coagulation process was initiated by adding the reagent, and the time until a fibrin clot formed was measured.

To determine the long-term stability of the various reagents, the reagents were stored in the liquid state at +2 to +8° C. over a period of up to 12 months. Samples of the reagents were taken each month, and the prothrombin time of the same reference plasma was determined. Lyophilized thromboplastin reagent of the same batch used to produce the various reagents was freshly reconstituted with distilled water and measured as control at each time.

Figure 1:
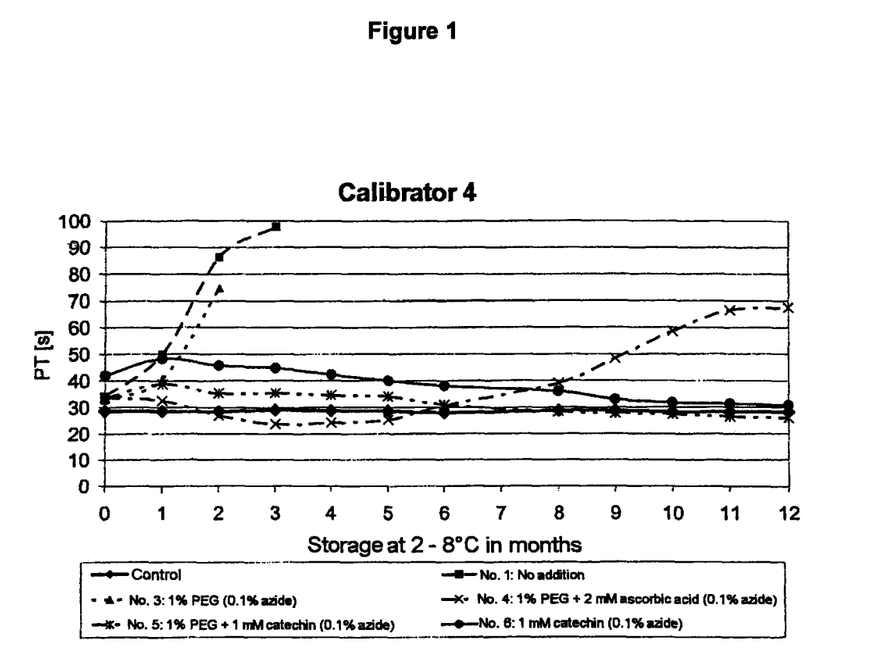
FIG. 1 Prothrombin times of a defined reference plasma (calibrator 4) with thromboplastin reagents stabilized in various ways during storage at +2 to +8° C. for 12 months (see example 1), (PEG=polyethylene glycol; azide=sodium azide).

FIG. 1 shows the prothrombin times of the various thromboplastin reagents over a period of 12 months. Stable prothrombin times with differences of less than 25% from the initial value at time to were achieved only with the thromboplastin reagents of the invention stabilized with catechin (Nos. 5 and 6). Only very different prothrombin times were provided by all the other reagents after 9 months at the latest (see No. 4). The sodium azide had no influence on the performance stability of the reagent. Reagent No. 2 (0.1% sodium azide; values not shown) behaved like reagent No. 1 (no addition). However, reagent No. 2 (0.1% sodium azide) had a distinctly less turbid appearance than reagent No. 1 (without sodium azide).

EXAMPLE 2

Determination of the Stability of Thromboplastin Reagents Stabilized with Catechin During Storage at 2-8° C. for 48 Weeks The following substances in the stated final concentration were added to the same thromboplastin reagent as in example 1:
7. 0.1% (w/v) sodium azide+1 mM catechin
8. 0.1% (w/v) sodium azide+0.5 mM catechin
9. 0.1% (w/v) sodium azide+0.1 mM catechin
10. 0.1% (w/v) sodium azide+0.5 mM catechin+1 mM L-ascorbic acid The various reagents were employed as described in example 1 for PT determination of a defined reference plasma (calibrator 1 of the PT-Multi Calibrator kit, Dade Behring Marburg GmbH, Marburg, Germany).

To determine the long-term stability of the various reagents, the reagents were stored in the liquid state at +2 to +8° C. over a period of up to 48 weeks. Samples of the reagents were taken every four weeks, and the prothrombin time of the same reference plasmas was determined. Lyophilized thromboplastin reagent of the same batch used to produce the various reagents was freshly reconstituted with distilled water and measured as control at each time.

Figure 2:
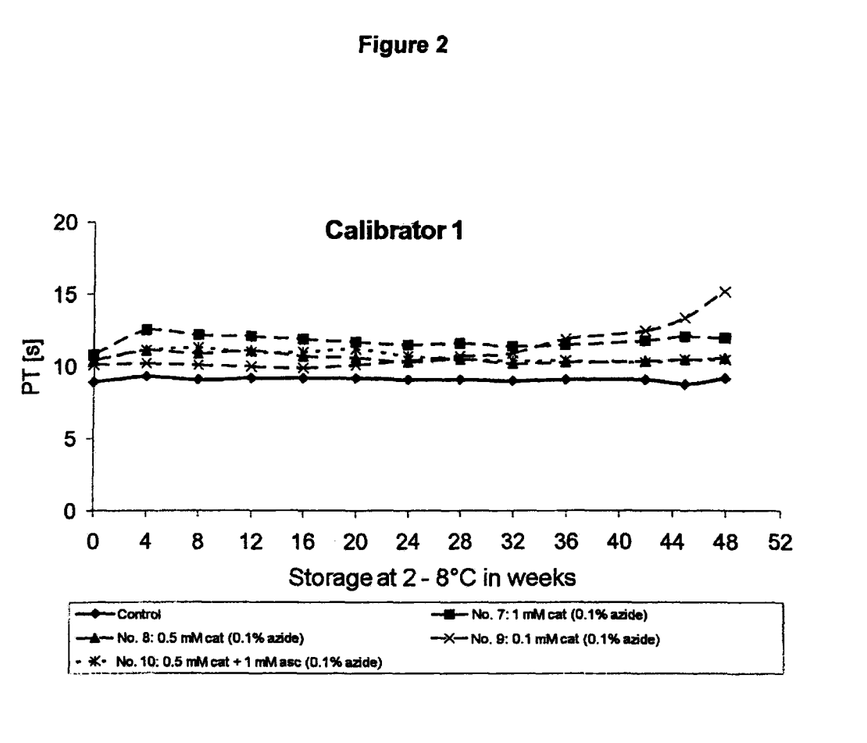
FIG. 2 Prothrombin times of a defined reference plasma (calibrator 1) with thromboplastin reagents stabilized in various ways during storage at +2 to +8° C. for 42 weeks (see example 2), (cat=catechin; asc=ascorbic acid; azide=sodium azide).

The storage test shows that a concentration of 0.1 mM catechin (reagent No. 9) is insufficient to stabilize the thromboplastin reagent for more than about 32 weeks at +2-+8° C. (FIG. 2). A concentration of 0.5 mM catechin, and the combination of 0.5 mM catechin and 1 mM L-ascorbic acid have the effect, however, of stabilizing the thromboplastin reagent over a period of at least 48 weeks (FIG. 2). The extent of the observed prolongation of the prothrombin time after addition of catechin is evidently concentration-dependent.

EXAMPLE 3

Determination of the Stability of Thromboplastin Reagents Stabilized with Various Polyphenols During Storage at 37° C. for 8 Weeks The following substances in the stated final concentration were added to the same thromboplastin reagent as described in example 1:
11. 0.1% (w/v) sodium azide+1 mM catechin
12. 0.1% (w/v) sodium azide+1 mM epicatechin
13. 0.1% (w/v) sodium azide+1 mM rutin
14. 0.1% (w/v) sodium azide+1 mM chlorogenic acid
15. 0.1% (w/v) sodium azide+2 mM chlorogenic acid The various reagents were employed as described in example 1 for PT determination of a defined reference plasma (calibrator 1 of the PT-Multi Calibrator kit, Dade Behring).

To determine the long-term stability of the various reagents, the reagents were stored in the liquid state at +37° C. for a period of up to 8 weeks. Samples of the reagents were taken after one, four and eight weeks, and the prothrombin times of the same reference plasma were determined. Lyophilized thromboplastin reagent of the same batch used to produce the various reagents was freshly reconstituted with distilled water and measured as control at each time.

Figure 3:
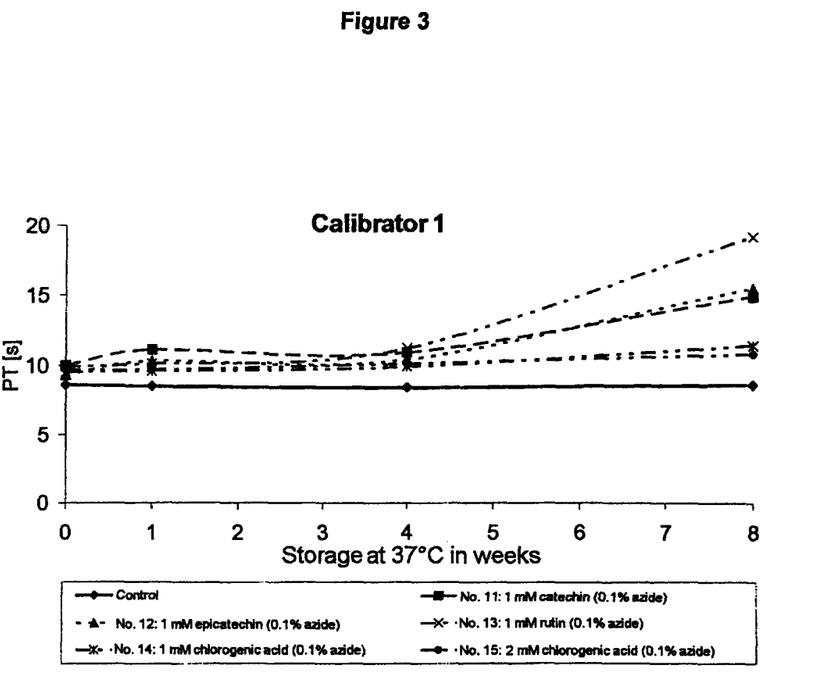
FIG. 3 Prothrombin times of a defined reference plasma (calibrator 1) with thromboplastin reagents stabilized in various ways during storage at +37° C. for 8 weeks (see example 3), (azide=sodium azide).
Figure 4:
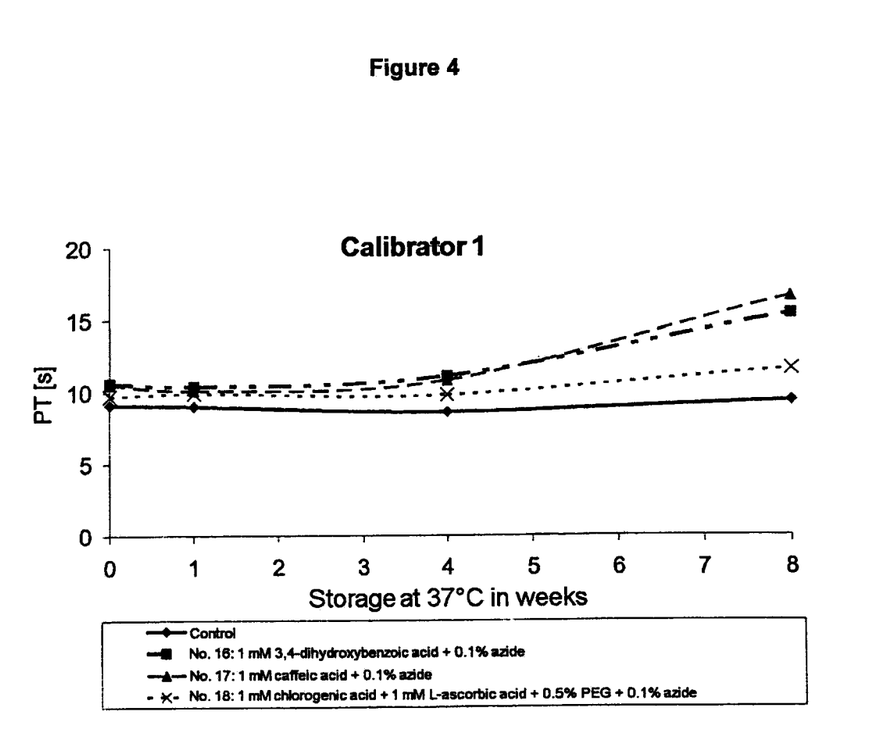
FIG. 4 Prothrombin times of a defined reference plasma (calibrator 1) with thromboplastin reagents stabilized in various ways during storage at +37° C. for 8 weeks (see example 4), (azide=sodium azide).

The accelerated stability investigation at +37° C. shows that the flavan-3-ol epicatechin (epimer of catechin), the flavonol glycoside rutin, and the hydroxycinnamic acid derivative chlorogenic acid are likewise suitable in comparable concentrations to catechin for stabilizing a thromboplastin reagent (FIG. 3). It was possible to stabilize the thromboplastin reagent particularly well by adding 2 mM chlorogenic acid.

EXAMPLE 4

Determination of the Stability of Thromboplastin Reagents Stabilized with Various Polyphenols During Storage at 37° C. for 8 Weeks The following substances in the stated final concentration were added to the same thromboplastin reagent as described in example 1:
16. 0.1% (w/v) sodium azide+1 mM 3,4-dihydroxybenzoic acid
17. 0.1% (w/v) sodium azide+1 mM caffeic acid
18. 0.1% (w/v) sodium azide+1 mM chlorogenic acid+1 mM L-ascorbic acid+0.5% PEG The various reagents were employed as described in example 1 for PT determination of a defined reference plasma (calibrator 1 of the PT-Multi Calibrator kit, Dade Behring).

To determine the long-term stability of the various reagents, the reagents were stored in the liquid state at +37° C. for a period of up to 8 weeks. Samples of the reagents were taken after one, four and eight weeks, and the prothrombin times of the same reference plasma were determined. Lyophilized thromboplastin reagent of the same batch used to produce the various reagents was freshly reconstituted with distilled water and measured as control at each time.

The accelerated stability investigation at +37° C. shows that the polyphenols 3,4-dihydroxybenzoic acid, caffeic acid and chlorogenic acid (Nos. 16-18) are suitable in the concentrations used for long-term stabilization of the lyophilized thromboplastin reagent. It was possible to stabilize the thromboplastin reagent particularly well by adding the combination of substances (No. 18).

EXAMPLE 5

Determination of the Stability of Thromboplastin Reagents Stabilized with a Plurality of Polyphenols During Storage at 37° C. for 8 Weeks The following substances in the stated final concentration were added to the same thromboplastin reagent as described in example 1:
19. 0.1% (w/v) sodium azide+0.5 mM catechin+0.5 mM chlorogenic acid
20. 0.1% (w/v) sodium azide+1 mM chlorogenic acid+0.5 mM rutin
21. 0.1% (w/v) sodium azide+0.5 mM chlorogenic acid+0.5 mM catechin+0.5 mM L-ascorbic acid The various reagents were employed as described in example 1 for PT determination of defined reference plasmas (K1 to K6, PT multicalibrators, Dade Behring). The calibration plots resulting therefrom were compared with one another.

To determine the long-term stability of the various reagents, the reagents were stored in the liquid state at +37° C. for a period of up to 8 weeks. Samples of the reagents were taken after four and eight weeks, and the prothrombin times of the same reference plasmas were determined. Lyophilized thromboplastin reagent of the same batch used to produce the various reagents was freshly reconstituted with distilled water and measured as control at each time.

Figure 5:
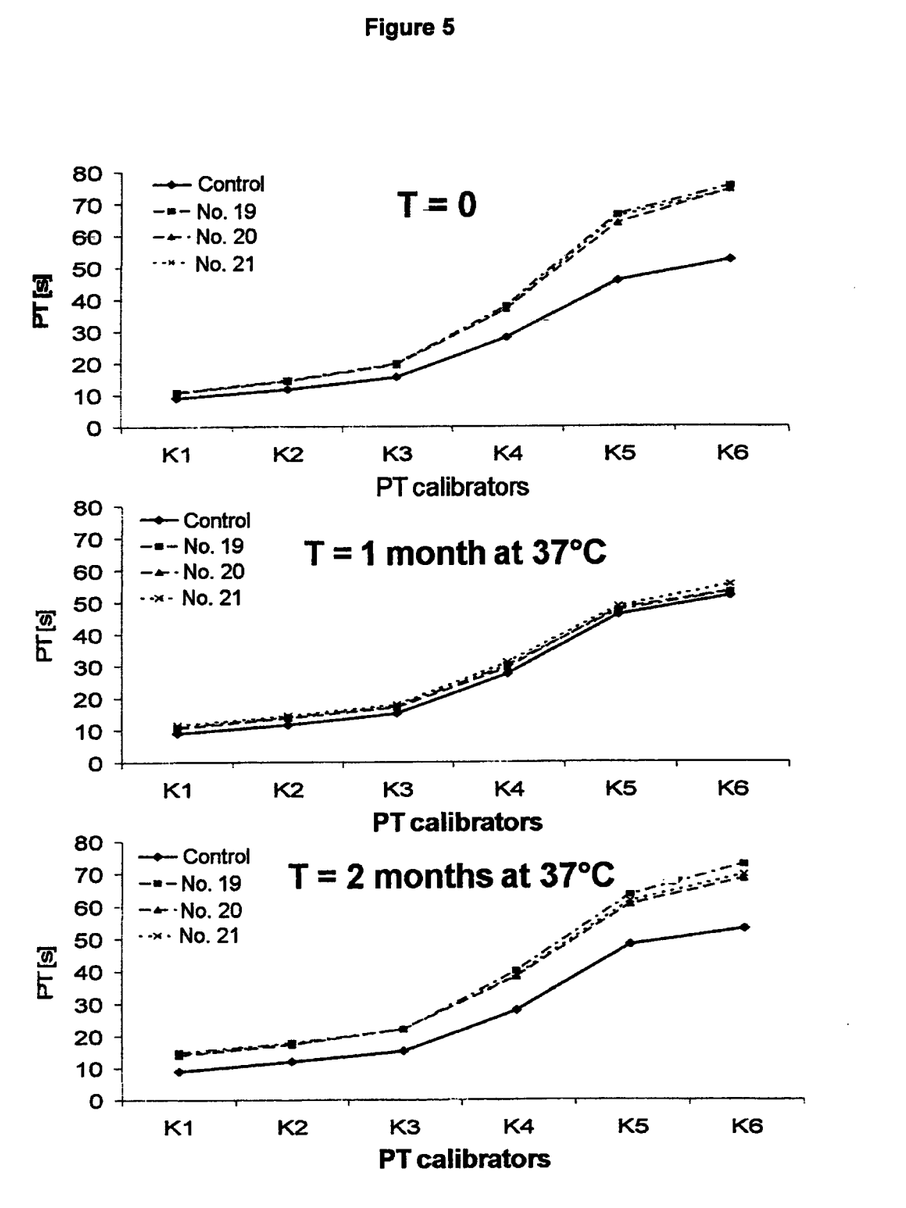
FIG. 5 Prothrombin times of defined reference plasmas (K1 to K6, PT Multi Calibrator Kit, Dade Behring Marburg GmbH) with thromboplastin reagents stabilized in various ways during storage at +37° C. for 8 weeks (see example 5).

The accelerated stability investigation at +37° C. shows that combinations of the polyphenols catechin, chlorogenic acid and rutin (Nos. 19-21) are suitable in the concentrations used for long-term stabilization of the lyophilized thromboplastin reagent (FIG. 5).

The invention claimed is:

1. A liquid thromboplastin reagent comprising isolated tissue factor, phospholipids, and at least one water-soluble polyphenol which has at least one catechol function, wherein the thromboplastin reagent is free of serum or plasma.

2. The reagent as claimed in claim 1, which comprises two or more water-soluble polyphenols, of which at least one has at least one catechol function.

3. The reagent as claimed in claim 1 or claim 2, which comprises at least one water-soluble polyphenol which has at least one catechol function, in a concentration from 0.15 to 10 mM.

4. The reagent as claimed in claim 1, wherein the at least one water-soluble polyphenol which has at least one catechol function is a flavonoid.

5. The reagent as claimed in claim 4, wherein the flavonoid is chosen from quercetin, rutin, myricetin, catechin, epicatechin, gallocatechin, epigallocatechin, epigallocatechin gallate, luteolin, delphinidin, petunidin, and cyanidin.

6. The reagent as claimed in claim 1 wherein the at least one water-soluble polyphenol which has at least one catechol function is a phenolic acid.

7. The reagent as claimed in claim 6, wherein the phenolic acid is chosen from gallic acid, p otocatechuic acid, caffeic acid, rosmarinic acid, chlorogenic acid, and caftaric acid.

8. The reagent as claimed in claim 1, which additionally comprises L-ascorbic acid.

9. The reagent as claimed in claim 8, which comprises L-ascorbic acid in a concentration from 0.1 to 10 mM.

10. The reagent as claimed in claim 1 or claim 8, which additionally comprises polyethylene glycol.

11. The reagent as claimed in claim 10, which comprises polyethylene glycol in a concentration from 0.1 to 5% (w/v).

12. The reagent as claimed in claim 1 or claim 8, which additionally comprises at least one substance having an antimicrobial activity.

13. The reagent as claimed in claim 12, wherein the at least one substance having antimicrobial activity is chosen from sodium azide and thymol.

14. The reagent as claimed in claim 13, which comprises sodium azide in a concentration of from 0.01% to 1% (w/v).

15. The reagent as claimed in claim 1 wherein the tissue factor is chosen from human recombinant tissue factor, animal recombinant tissue factor, recombinant rabbit tissue factor, natural human tissue factor from a tissue extract, and animal tissue factor from a tissue extract.

16. The reagent as claimed in claim 3, wherein the concentration of the at least one water-soluble polyphenol is 0.5 to 2 mM.

17. The reagent as claimed in claim 9, wherein the concentration of L-ascorbic acid is from 0.5 to 1 mM.

18. The reagent as claimed in claim 11, wherein the concentration of polyethylene glycol is from 0.25 to 1% (w/v).

19. The reagent as claimed in claim 14, wherein the concentration of sodium azide is 0.1% (w/v).

20. The reagent as claimed in claim 12, which additionally comprises polyethylene glycol.

21. The reagent as claimed in claim 1, wherein the reagent is stable for at least 12 months at a temperature ranging from +2° C. to +8° C. as determined by a difference of less than 25% in prothrombin time.

22. The reagent as claimed in claim 1, wherein the reagent is stable for at least 4 weeks at a temperature of +37° C. as determined by a difference of less than 25% in prothrombin time.

* * * * *